United States Patent [19]

Ishida et al.

[11] 4,393,304
[45] Jul. 12, 1983

[54] GAS ANALYZER OF THE FLUID MODULATION TYPE

[75] Inventors: Kozo Ishida; Hiroji Kohsaka, both of Kyoto, Japan

[73] Assignee: Horiba, Ltd., Kyoto, Japan

[21] Appl. No.: 235,739

[22] Filed: Feb. 18, 1981

[30] Foreign Application Priority Data

Mar. 1, 1980 [JP] Japan ............................. 55-27076

[51] Int. Cl.³ .................................................. G01J 1/00
[52] U.S. Cl. ................................ 250/343; 250/344; 73/863.44
[58] Field of Search ............... 250/338, 343, 344, 345, 250/346; 356/436, 437; 73/863.11, 863.44

[56] References Cited

U.S. PATENT DOCUMENTS

| | | | |
|---|---|---|---|
| 3,699,814 | 10/1972 | Kaufmann | 73/863.11 |
| 3,920,993 | 11/1975 | Cederstrand et al. | 250/345 |
| 4,090,078 | 5/1978 | Heim | 250/343 |
| 4,232,223 | 11/1980 | Ohnishi et al. | 250/343 |
| 4,256,964 | 3/1981 | Ishida et al. | 250/345 |

Primary Examiner—Alfred E. Smith
Assistant Examiner—Janice A. Howell
Attorney, Agent, or Firm—Wenderoth, Lind & Ponack

[57] ABSTRACT

A gas analyzer of the fluid modulation type includes at least one cell, structure for alternately introducing a sample gas to be analyzed and a reference gas into the cell, a detector for analyzing a property of the sample gas, and an arrangement for alternately discharging the sample gas and the reference gas from the cell. A critical flow device is located in the discharging arrangement. A pump is located in the discharging arrangement and has a capacity for operating the critical flow device under conditions of critical gas flow, thereby maintaining the gas passing through the critical flow device and the cell at a constant flow rate.

10 Claims, 9 Drawing Figures

GAS ANALYZER OF THE FLUID MODULATION TYPE

BACKGROUND OF THE INVENTION

The present invention relates to a gas analyzer, for example an infrared gas analyzer, of fluid modulation type, in which a test or sample gas and a standard gas are alternately introduced at predetermined periods of time or intervals or cycles into at least one cell. For example, the test gas and standard gas may alternately be introduced into a single cell or into a pair of cells. That is to say, when the test gas is introduced into one cell, the standard gas is introduced into the other cell.

In a gas analyzer of the fluid modulation type, changes in the variation of the energy detected by a detector are influenced by a change in the time required for a displacement of the test gas contained in a cell by the standard gas, and vice versa. For example, the displacement of these gases in a cell occurs in a pulse-like manner. The detector thus operates at highest modulation efficiency, which is theoretically ideal, when the flow rate K of the test gas and the standard gas is infinitely great. On the contrary, the detector operates at a modulation efficiency of zero when the flow rate K of the test gas and the standard gas is equal to one half of the volume of a cell per gas displacement period (see FIG. 1).

Now assuming that diffusion does not take place at the boundary between the standard gas and the test gas and that displacement is carried out immediately before a cell, the modulation efficiency S can be expressed by the following equation if it is assumed that the modulation efficiency is an integral value of the displacement or change of the gas in the cell (see FIG. 2):

$$S = 1 - \tfrac{1}{4}K \quad (1)$$
$$= (QT - V)/QT$$

wherein:
$K = QT/2V$;
$K \geq 0.5$;
Q = Flow rate of the test gas and the standard gas per unit time;
V = Volume of the cell; and
T = Modulation period (two times the gas-displacement period).

FIG. 3 shows dimensionless output-flow rate characteristics for cells having various shapes. The shapes of cells graphed or plotted in FIG. 3 are as follows:
. - - - $\phi 8 \times 100$; ▲ - - - $\phi 10 \times 100$; ○ - - - $\phi 12 \times 100$; □ - - - $\phi 12 \times 50$ (mm). It will be clearly understood that the ideal curve from the above described equation (1), as shown in FIG. 2 and as shown by the curve in FIG. 3, is sufficiently identical with practical output-flow rate characteristics, as shown by the plottings in FIG. 3. This shows that the gas displacement efficiency has an influence upon the output from the detector. Also, a differential value of this curve gives the value of the influence upon the output of the detector by variations or changes of the flow rate of the test gas and the standard gas.

Moreover, FIG. 4 and FIG. 5 are graphs showing the test results of changes in flow rate for a double cell of 3 mm and 35 mm, respectively. Curves a, a' show the detector outputs for various values of the flow rate of span gas, i.e. a gas having a known concentration used for calibration in place of a sample gas, using nitrogen as the standard gas at a constant flow rate of 0.5 liter/min. Hereinafter b, b'; c, c'; d, d'; e, e'; and f, f' show the detector outputs employing nitrogen as the standard gas at constant flow rates of 1.0 liter/min, 2.0 liter/min, 3.0 liter/min, 4.0 liter/min and 5.0 liter/min, respectively. It clearly will be understood that the variations in the flow rate of the gas greatly influences the output of the analyzer.

As clearly understood from the above description, in a gas analyzer of the fluid modulation type, the maintenance of a constant flow rate of gas introduced into the cell is most important for eliminating errors in the output of the analyzer.

In a conventional analyzer of this type, a constant pressure regulator and a capillary tube are used in order to attempt to introduce the gas into the cell at a constant flow rate. It has, however, been found that the accurate maintenance of a constant flow rate over a long period of time is impossible for the following reasons:

a. poor mechanical reproducibility of a constant pressure regulator;

b. time change of pressure adjustment due to contamination of the constant pressure regulator; and P. c. choking and contamination of a capillary tube or the like, with the result that indication errors are unavoidable.

SUMMARY OF THE INVENTION

With the above discussion in mind, it is an object of the present invention to provide a gas analyzer of the fluid modulation type which overcomes the prior art disadvantages by ensuring constant gas flow rates and thereby much more accurate analysis.

This object is achieved in accordance with the present invention by the provision of a gas analyzer of the fluid modulation type and including at least one cell, a device for alternately introducing a sample gas to be analized and a reference gas into the cell, a detector for analizing a property of the sample gas, and an arrangement for alternatively discharging the sample gas and the reference gas from the cell, the improvement including a critical flow device located in the discharge arrangement, and a pump device, located in the discharging arrangement, for operating the critical flow device under conditions of critical gas flow and for thereby maintaining the gas passing through the critical flow device and the cell at a constant flow rate.

Preferably, the critical flow device comprises a critical flow venturi.

Preferably, the introducing structure comprises a supply line for the sample gas, a supply line for the reference gas, and a rotary valve connected to the supply lines and to the cell.

In one embodiment of the present invention, the gas analyzer of the fluid modulation type includes a single cell. A gas exhaust conduit is connected to the cell, the critical flow venturi is connected to the gas exhaust conduit, and the pump is connected to the gas exhaust conduit at a position therein downstream of the critical flow venturi, i.e. the pump is connected to the discharge or expansion side of the critical flow venturi.

In accordance with a further embodiment of the present invention, the gas analyzer of the fluid modulation type may include first and second cells, and the introducing structure introduces the sample gas into the first cell while introducing the reference gas into the second cell, and vice versa. A first gas exhaust conduit is connected to the first cell, and a second gas exhaust conduit is connected to the second cell. First and second critical flow venturies may be connected to the first and second gas exhaust conduits respectively, and first and second pumps may be provided in the first and second gas exhaust conduits, respectively, at positions therein downstream of the first and second critical flow venturies, i.e. at positions connected to the discharge or expansion sides of the respective venturies. Alternatively, a single critical flow venturi may be connected to both the first and second gas exhaust conduits, and a single pump may be connected to the single critical flow venturi at a position downstream thereof, i.e. connected to the discharge or expansion side of the single critical flow venturi. Preferably, the pump or pumps maintain the flow rates of the sample gas and the reference gas through both the first and second cells constantly equal. That is, the flow rate of the sample gas through the first cell equals the flow rate of the reference gas through the second cell, and such flow rates equal the flow rate of the sample gas through the second cell and the flow rate of the reference gas through the first cell.

BRIEF DESCRIPTION OF THE DRAWINGS

Other objects, features and advantages of the present invention will be apparent from the following detailed description thereof, taken with the accompanying drawings, wherein.

DETAILED DESCRIPTION OF THE INVENTION

Figure 1:
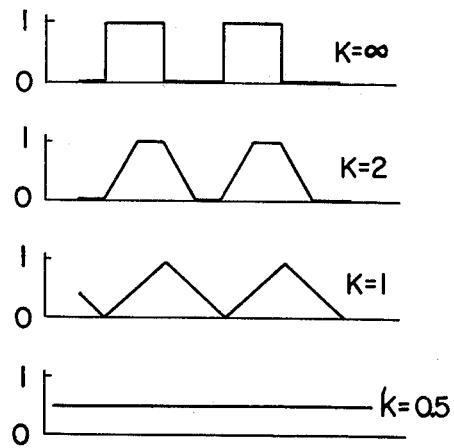
FIG. 1 is a graph showing the shapes of gas displacement waves in a gas analyzer of the fluid modulation type.
Figure 2:
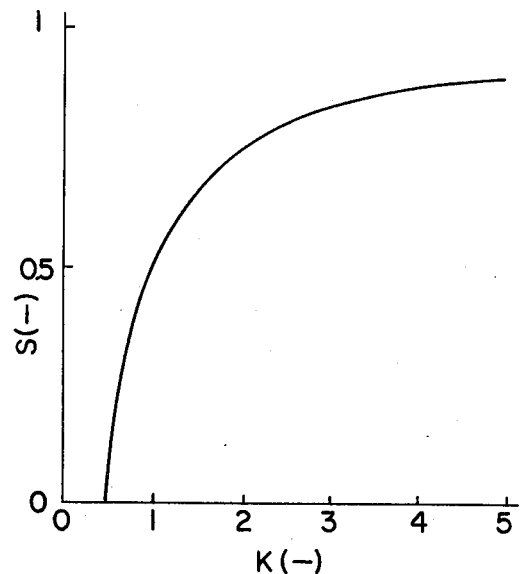
FIG. 2 is a graph illustrating ideal modulation efficiency.
Figure 3:
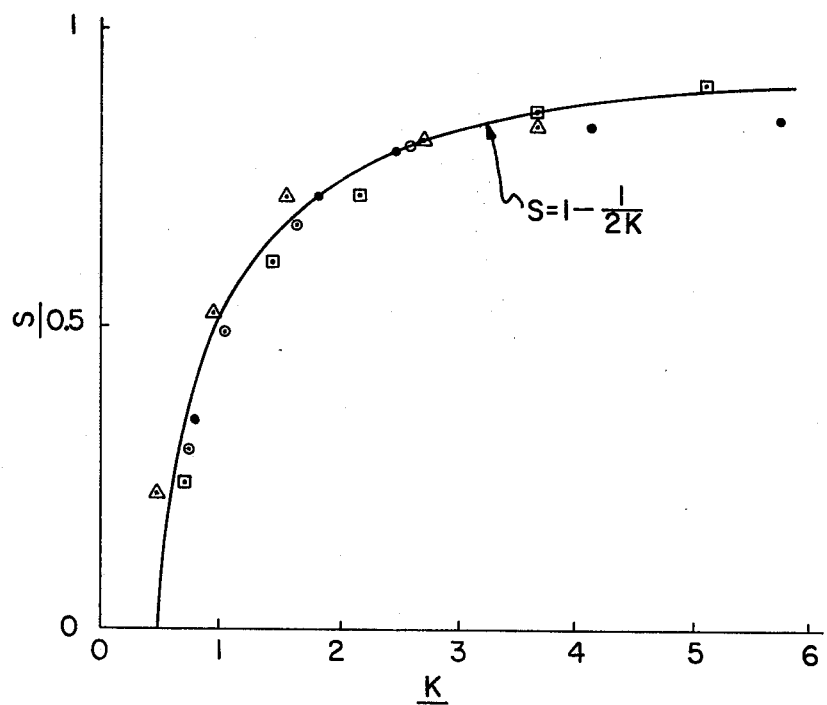
FIG. 3 is a graph illustrating actual output-flow rate characteristics.
Figure 4:
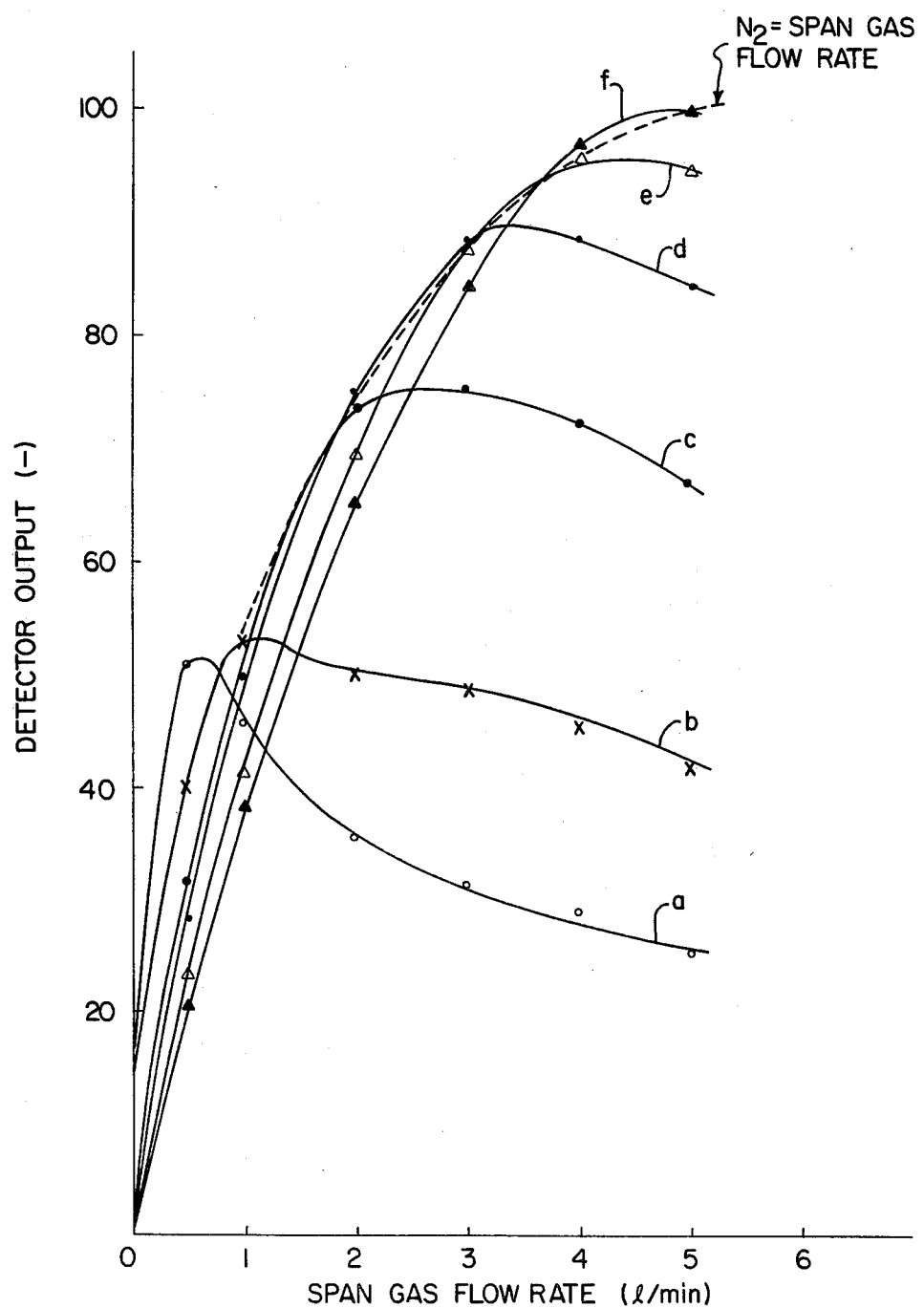
FIG. 4 and FIG. 5 are graphs illustrating test results of variations of flow rate for a double cell of 3 mm and 35 mm, respectively.
Figure 5:
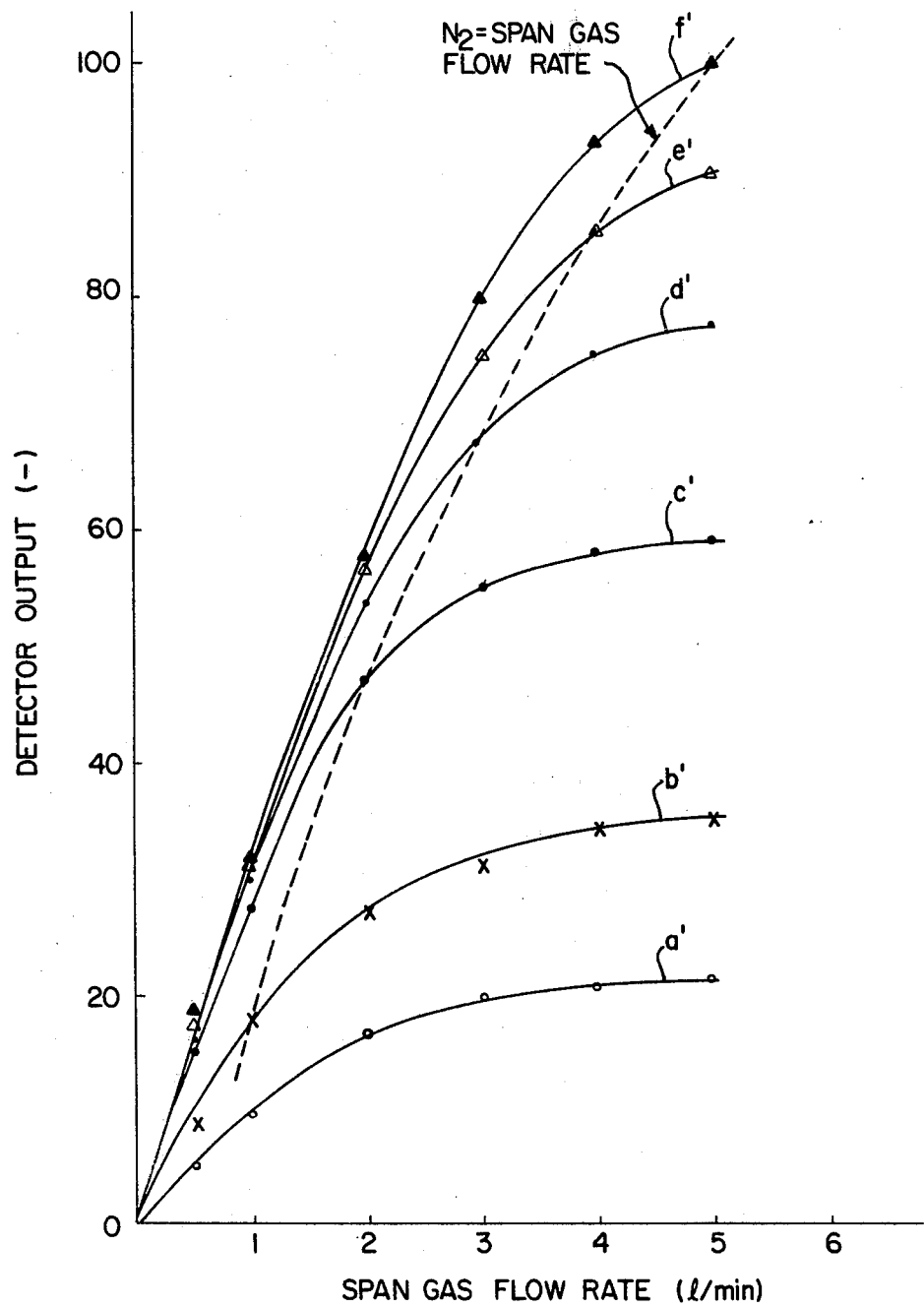
Figure 6:
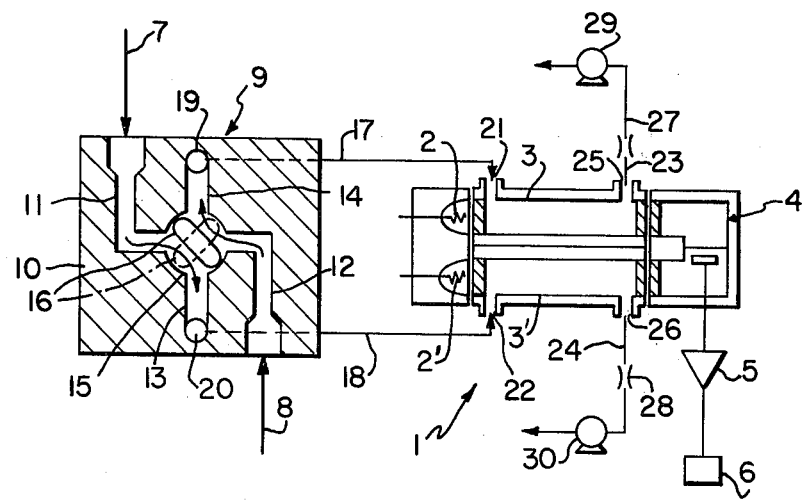
FIG. 6 is a diagrammatic sectional view of a gas analyzer of the double cell type according to a first embodiment of the present invention.

With reference now to FIG. 6, a first embodiment of a gas analyzer of the fluid modulation type in accordance with the present invention will be described. Specifically, there is illustrated an infrared gas analyzer of the double cell, fluid modulation type including a pair of light sources 2, 2', a pair of cells 3, 3', a detector 4, an amplifier 5 and a meter 6. It is to be understood that the scope of the present invention is not intended to be limited to an infrared gas analyzer, but that the present invention is equally applicable to other known types of gas analyzers. Furthermore, the particular configuration and construction of detector 4 does not in and of itself constitute a feature of the present invention, but rather the invention is intended to be employable with any type of such detector known in the art for use in conventional gas analyzers of the fluid modulation type. Thus, gas analyzers of the fluid modulation type are known in the art, and it is intended that the novel features of the present invention may be employable with any such type analyzer. In this regard, gas analyzers of the fluid modulation type are disclosed in U.S. Pat. No. 4,232,223 and in U.S. Pat. No. 4,256,964, the disclosures of which are hereby incorporated by reference.

Structure for alternately introducing sample or test gas and reference or standard gas into cells 3, 3' preferably comprises a rotary valve 9 including a block 10 having therein a gas conduit change-over chamber 15 within which rotates a disc valve body 16. Body 16 is rotated, for example by means of a motor, not shown, at constant and equal time intervals or cycles. A test gas supply conduit 7 is connected to a gas conduit 11 which is turn connected to chamber 15. A standard gas supply conduit 8 is connected to a gas conduit 12 which is in turn connected to chamber 15. Gas conduits 13 and 14 are connected to chamber 15 and are also connected to exhaust ports 19, 20, respectively. Gas conduits 17 and 18 are connected to gas exhaust ports 19, 20, respectively, and also to inlet ports 21, 22 provided in cells 3, 3', respectively. Exhaust conduits 23, 24 are respectively connected to exhaust ports 25, 26 of cells 3, 3', respectively.

In the position of the disc valve body 16 shown by solid lines in FIG. 6, test gas is introduced from conduit 7 into conduit 11, and passes from chamber 15 through port 20, conduit 18 and port 22 into cell 3', and then exhausts through port 26 and conduit 24. Simultaneously, reference or standard gas is introduced from conduit 8 into conduit 12, and then passes through chamber 15, conduit 14, port 19, conduit 17 and port 21 into cell 3, and then exhausts through port 25 and conduit 23. At a predetermined timed interval, disc 16 is moved to the position shown by dashed lines in FIG. 6, such that the flows of the test gas and standard gas are reversed, i.e. such that test gas from conduit 7 flows into cell 3, and standard gas from conduit 8 flows into cell 3'. Continued rotation of disc 16, at predetermined constant time intervals, will result in continuous alternative feeding in the manner described above.

In accordance with the present invention, the flow rates of the gases in cells 3, 3' are maintained constant by the use of critical flow devices 27, 28 in conduits 23, 24, respectively, and by means of pumps 29, 30 for respectively operating critical flow devices 27, 28 at conditions of critical gas flow. As employed herein, the term "critical flow device" is intended to encompass all types of devices capable of actuation and operation under conditions of critical gas flow, for example a critical flow venturi, a critical flow nozzle, and the like. Such terms and the structures intended thereby will be readily apparent to those skilled in the art. It is specifically preferred in accordance with the present invention that the critical flow devices 27, 28 be critical flow venturies, such as disclosed in U.S. Pat. No. 3,699,814, the disclosure of which is incorporated herein by reference.

A predetermined constant flow rate of gas passes through critical flow devices 27, 28, since such devices are constructed and operate under conditions of critical gas flow, during operation of the gas analyzer. Further, pumps 29, 30 have sufficient capacity to ensure operation of critical flow devices 27, 28 under conditions of critical gas flow. Accordingly, the flow rates of the gases passing through cells 3, 3' is always maintained constant by the critical flow devices 27, 28 operating under conditions of critical gas flow. Preferably, the flow rate of the gas passing through the critical flow device 27 is equal to the flow rate of the gas passing through the critical flow device 28, and consequently the flow rate of the gas passing through cell 3 will be equal to the flow rate of the gas passing through cell 3'.

Figure 7:
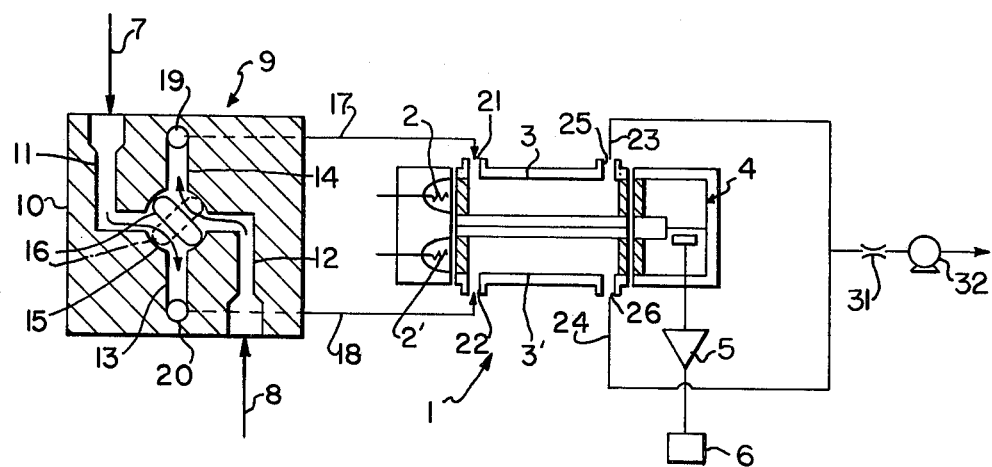
FIG. 7 is a diagrammatic sectional view of a gas analyzer similar to FIG. 1, but of a second embodiment of the present invention.

Reference will now be made to FIG. 7 which illustrates a modification of the arrangement of FIG. 6. Thus, the structure of FIG. 7 is identical with the structure of FIG. 6, with the exception that a single critical flow device 31, such as a critical flow venturi, and a single pump 32 are connected to both of conduits 23, 24. By this arrangement, a single pump 32 and a single critical flow device 31 operate to maintain the flow rate of the test gas and the standard gas through cells 3, 3' constant.

Figure 8:
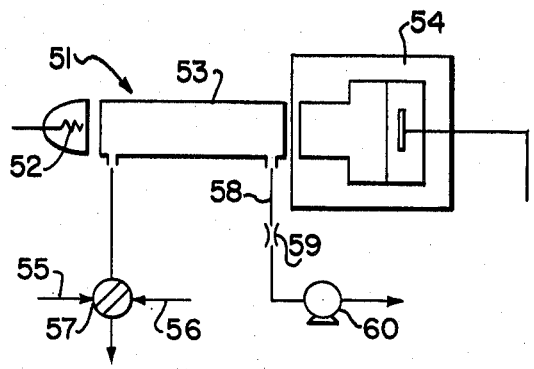
FIG. 8 is a diagrammatic view of a gas analyzer of the single cell type according to a further embodiment of the present invention.

The concept of the present invention is also applicable to a gas analyzer of the fluid modulation type employing only a single cell. Such an arrangement will now be described with reference to FIG. 8. Thus, an infrared gas analyzer 51 of the single cell, fluid modulation type includes a light source 52, a single cell 53, a detector 54, a conduit 55 for introducing test gas, a conduit 56 for introducing standard gas, a rotary valve 57 for alternately introducing the test gas and standard gas into cell 53, a gas exhaust conduit 58 for discharging the gas from cell 53, a critical flow device 59, such as a critical flow venturi, connected in conduit 58, and a pump 60 connected downstream of critical flow device 59, i.e. at the discharge or expansion side thereof. In this embodiment, as in the embodiments of FIGS. 6 and 7, pump 60 causes critical flow device 59 to operate under conditions of critical gas flow. Thus, the flow rate of the test gas and the flow rate of the standard gas alternately introduced into single cell 53 at predetermined time periods by rotary valve 57 will be maintained constant.

As will be apparent from the above discussion, in accordance with the present invention, the flow rates of gases through cells of a gas analyzer of the fluid modulation type are maintained constant by providing a critical flow device in the gas exhaust of the cells, and by operating such critical flow device under conditions of critical gas flow. The critical flow device is more difficult to strain and choke, and consequently will enable the alternate introduction of the test gas and standard gas into the cells at desired constant flow rate for a longer period of time than known capillary tubes. That is, the gas will pass remarkably fast through the critical flow device. The result of such feature is that errors in the detection or analysis of the test gas will substantially be eliminated, in that there will no longer be a variation in the flow rate, such flow rate variation effecting accuracy of detection as indicated above. Additionally, in accordance with the present invention the critical flow device is a critical flow venturi which may be operated under conditions of critical gas flow by means of a pump having a relatively low capacity, since a critical flow venturi has a superior pressure recovery characteristic.

Figure 9:
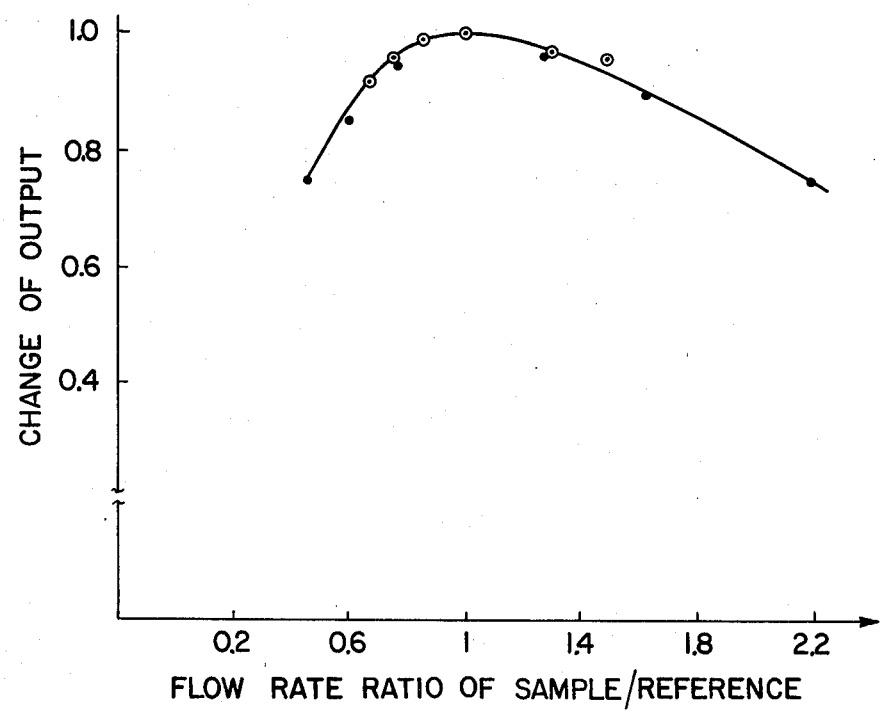
FIG. 9 is a graph showing the relationship between the flow rate ratio of the test gas to the standard gas and the change in detector output.

FIG. 9 is a graph showing the relationship between the ratio of the flow rate of the test or sample gas to the flow rate of the standard or reference gas and the change of output for a gas analyzer of the double cell type. It will be readily apparent that when the flow rate ratio is unity (that is, when the flow rate of the test gas is equal to the flow rate of the standard gas), variation in analyzer output is minimum (i.e. unity).

Although the present invention has been described and illustrated with respect to preferred features thereof, it is to be understood that various modifications or alterations may be made to the specifically described arrangements without departing from the scope of the present invention.

We claim:

1. In a gas analyzer of the fluid modulation type and including at least one cell, means for alternatively introducing a sample gas to be analyzed and a reference gas into said cell, detector means for analyzing a property of said sample gas, and means for alternately discharging said sample gas and said reference gas from said cell, the improvement comprising:

a critical flow device located in said discharging means; and pump means, located in said discharging means, for operating said critical flow device under conditions of critical gas flow and for thereby maintaining said gas passing through said critical flow device and said cell at a constant flow rate.

2. The improvement claimed in claim 1, wherein said critical flow device comprises a critical flow venturi.

3. The improvement claimed in claim 1, wherein said introducing means comprises a supply line for said sample gas, a supply line for said reference gas, and a rotary valve connected to said supply lines and to said cell.

4. The improvement claimed in claim 1, wherein said at least one cell comprises a single cell, and wherein said discharging means comprises a gas exhaust conduit connected to said cell, said critical flow device is connected to said gas exhaust conduit, and said pump means is connected to said gas exhaust conduit at a position therein downstream of said critical flow device.

5. The improvement claimed in claim 1, wherein said at least one cell comprise first and second cells, and wherein said introducing means comprises means for introducing said sample gas into said first cell while introducing said reference gas into said second cell, and vice versa, and said discharging means comprises a first gas exhaust conduit connected to said first cell and a second gas exhaust conduit connected to said second cell.

6. The improvement claimed in claim 5, wherein a first critical flow device is connected to said first gas exhaust conduit and a second critical flow device is connected to said second gas exhaust conduit.

7. The improvement claimed in claim 6, wherein said pump means comprises a first pump connected to said first gas exhaust conduit at a position therein downstream of said first critical flow device, and a second pump connected to said second gas exhaust conduit at a position therein downstream of said second critical flow device.

8. The improvement claimed in claim 5, wherein said critical flow device is connected to both said first and second gas exhaust conduits.

9. The improvement claimed in claim 8, wherein said pump means comprises a single pump connected to said single critical flow device downstream thereof.

10. The improvement claimed in claim 7 or claim 9, wherein said pump means maintains the flow rates of said sample gas and said reference gas in both said first and second cells constantly equal.

* * * * *